United States Patent

Abercrombie et al.

[11] Patent Number: 5,860,431
[45] Date of Patent: Jan. 19, 1999

[54] APPLICATOR FOR COLORING HAIR OR FIBERS AND METHODS FOR MAKING AND USING SAME

[76] Inventors: Tracy Hill Abercrombie, 1229 ½ Smithwood Dr., Los Angeles, Calif. 90035; Douglas M. Whitaker, 8000 Turtle La., Ooltewah, Tenn. 37363

[21] Appl. No.: 839,678

[22] Filed: Apr. 15, 1997

[51] Int. Cl.⁶ .......................................... A61K 7/13
[52] U.S. Cl. ............................. 132/208; 132/221
[58] Field of Search .................... 132/208, 221, 132/222, 108, 109, 110; 401/54; 424/62, 70.6

[56] References Cited

U.S. PATENT DOCUMENTS

| | | | |
|---|---|---|---|
| 2,299,985 | 10/1942 | Hudson | 132/221 |
| 4,206,195 | 6/1980 | Bolich, Jr. et al. | 424/70.6 |
| 4,271,272 | 6/1981 | Strickman et al. | 424/62 |
| 4,344,930 | 8/1982 | Mac Rae et al. | 424/62 |
| 4,594,362 | 6/1986 | Smith et al. | 424/62 |
| 4,658,839 | 4/1987 | Dallal et al. | 132/221 |
| 5,002,075 | 3/1991 | Kellett et al. | 132/108 |
| 5,121,762 | 6/1992 | Dipinto et al. | 132/221 |
| 5,146,937 | 9/1992 | Lefebvre | 132/208 |

FOREIGN PATENT DOCUMENTS 2140682  12/1984  United Kingdom .................. 132/208

*Primary Examiner*—Todd E. Manahan
*Attorney, Agent, or Firm*—Albert O. Cota

[57] ABSTRACT

An applicator for transferring color-altering material from a substrate to hair or fibers, and methods for making and using the same. The applicator includes a color-altering dye material adhered to one surface of the substrate. The substrate is preferably flexible and thin, and made of a material such as a foil, a paper composition or a synthetic polymer. The substrate is further conformable to the shape of a human hand. The dye material is soluble in water and water-activated, and is carried by a portion of the substrate. Two processes for fabricating the applicators are disclosed. Each applicator carries a dye material which has a specific color. The applicators can be packaged singly, or together as a kit with the color of dye on the applicators being the same, different, or a combination thereof. Use of an applicator requires wetting the hairs or fibers, and then applying a substrate to the hairs or fibers. Next, the user wraps the substrate about the bundle of hair or fibers, and firmly squeezes and/or wipes the encircling substrate relative to the bundle of fibers or hair.

30 Claims, 3 Drawing Sheets

APPLICATOR FOR COLORING HAIR OR FIBERS AND METHODS FOR MAKING AND USING SAME

BACKGROUND OF THE INVENTION

1. Field of the Invention

The present invention relates to processes and devices for coloring hair or fibers, and more particularly to apparatus for applying coloring material to hairs on the body or fibers in textile materials, including methods for making and using the apparatus.

2. Description of the Related Art

Apparatus and processes for applying color-altering materials, such as dyes, to hair or fibers for the purpose of temporarily covering or permanently dyeing such is well-known in the prior art. In the case of hair, such as human hair, the purpose typically is to cover unsightly or undesired indicators of aging. In the case of fibers, such as textile fibers, the purpose might be to cover stains or to resurrect old and faded products.

Typically, the color of the hair or fibers can be altered through the use of rinses, sprays, lotions, or creams. The coloring material usually takes the form of a dye, or a dye and bleach combination, and is applied in a step-by-step manner, oftentimes including the application of heat or requiring waiting a period of time sufficient for reaction of chemicals to take place.

Against this background of known technology, the applicants have developed a new, more efficient, speedier, and cost-effective technique for applying coloring material to hair or fibers which can be performed outside the confines of a salon (hair) or factory (textiles), and by persons of little or no training.

More particularly, the applicants have invented a dye-bearing substrate and a method of making and using such. The substrate is constructed in such a manner as to enable the transfer of dye material to the hair or fibers without requiring the user to mix or touch the dye or other chemicals carried by the substrate.

OBJECTS AND SUMMARY OF THE INVENTION

It is therefore an object of the present invention to provide novel color applicators on each of which is affixed a hair or fiber coloring dye, and methods for making and using such applicators, while overcoming many drawbacks and disadvantages of other color applicators known in the art.

Another object of the invention is to provide novel methods for securing water-activated dye on a thin, flexible, substrate, the dye residing on the substrate in a predetermined pattern or configuration.

Still another object of the invention is to provide an applicator tool for transferring dye from one surface to another, where the one surface comprises a substrate to which the dye is affixed and the other surface comprises the exterior of fibers, such as human hair or textiles, the substrate preferably comprising a flexible material, such as a thin sheet or foil of paper, plastic or metal, configured for conformable support in the human hand.

Still another object of the invention is to provide a plurality of applicator tools, each comprising a flexible substrate conformable to a human hand on one surface of which is secured a dye material, two or more of the plurality of tools preferably being packaged together as a set or kit.

These and other objects of the present invention are achieved in accordance with the present invention by a color applicator which includes a dye material adhered to one surface of a substrate. The substrate is preferably flexible and thin, and made of a material such as a foil, a paper composition or a synthetic polymer. The substrate is further conformable to the shape of a human hand. The dye material is preferably soluble in water and water-activated, and is carried by a portion of the substrate. Two processes for fabricating the applicators are disclosed.

Each applicator carries a dye material which has a specific color. The applicators are packaged singly, or they may be packaged together as a kit with the color of dye on the applicators being the same, different, or a combination thereof.

Use of an applicator involves wetting the bundle of hairs or fibers to be colored, and then interposing a substrate between the user's hand and the bundle of hair or fibers, cradling the substrate in the hand so that the substrate can conform to the shape of the hand. Next, the user wraps the substrate about the bundle of hair or fibers, and firmly squeezes and/or wipes the encircling substrate relative to the bundle of fibers or hair.

DETAILED DESCRIPTION OF THE INVENTION

Figure 1:
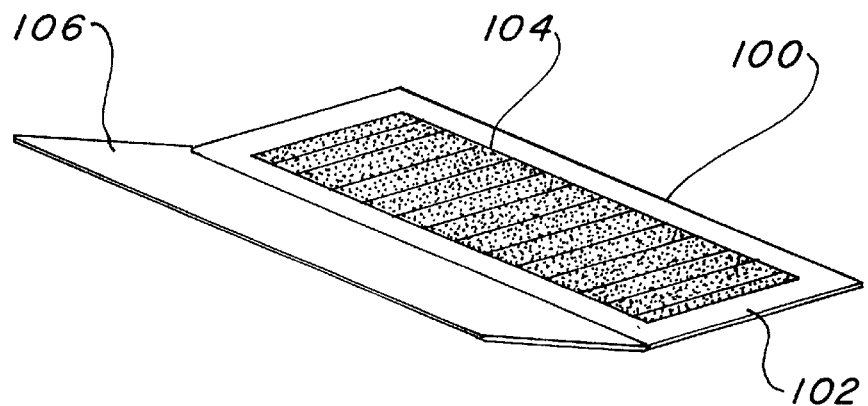
FIG. 1 depicts a color applicator in accordance with the present invention.

FIG. 1 shows an applicator 100 according to the present invention, including a substrate having a first portion 102 on which a layer 104 of dye material is deposited. The substrate may include a second portion 106 contiguous with the first portion, on which no dye material is deposited. Portion 106 preferably folds over the portion 102 as a covering therefor.

The substrate is preferably a thin, flexible, conformable material, such as paper or paper composition, plastic or a foil (e.g., metal, saran, etc.) The dye material is preferably a dry, particulate (or powdered), color-altering composition or compound that is water soluble and water-activated.

Generally, the present invention contemplates fabrication of the applicator by adhering dye material to a substrate using a binder material.

Figure 2:
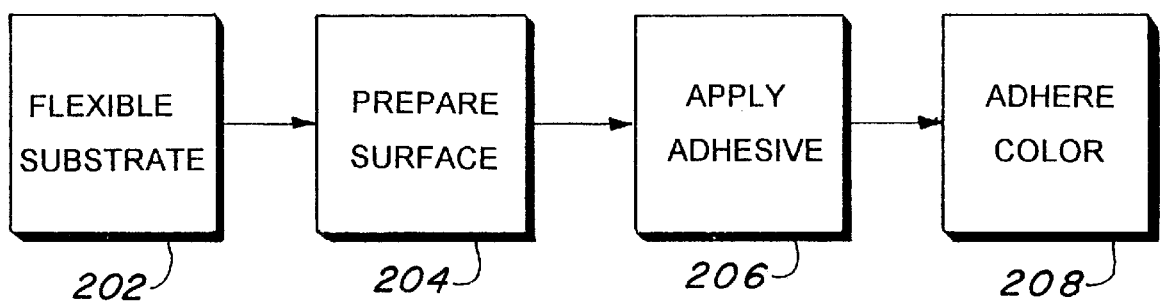
FIG. 2 is a flow chart showing a sequence of steps of a first process for making a color applicator in accordance with the teachings of the present invention.

FIG. 2 of the drawings is a flow chart depicting a sequence of that must be followed to carry out one process for obtaining an applicator of the type shown in FIG. 1.

The first block 202 of FIG. 2 represents the need to provide a substrate which can be a thin, flexible sheet of material. This material can be paper, plastic, or a metal foil.

The second block 204 represents the step of preparing one surface of the substrate for receipt of a first adhesive material. The preparation contemplated for this step involves smoothing and cleaning the surface.

The third block 206 represents the step of applying the adhesive material to the one surface of the substrate. This is accomplished by spraying or brushing the adhesive onto the one surface of the substrate. The adhesive material can include an adhesive composition, such as glue or other similar adherents. The purpose of the adhesive material is to provide a tacky coating on the one surface of the substrate.

The fourth block 208 represents the step of covering the adhesive coating with a powdered or particulate, water soluble and water-activated, dye material. This can be accomplished by dusting or otherwise depositing the dye material on the adhesive coating.

The tacky adhesive coating, and hence the dye material, is preferably applied over a substantially geometrical pattern, such as a rectangle or square area. The coating may also be applied to a plurality of regions having shapes or configurations which are contiguous or spaced from one another with regularity or randomness. The coating configurations are designed to provide delivery or transfer of the dye material to a bundle of hair or fibers in a maximized, efficient, manner.

Figure 3:
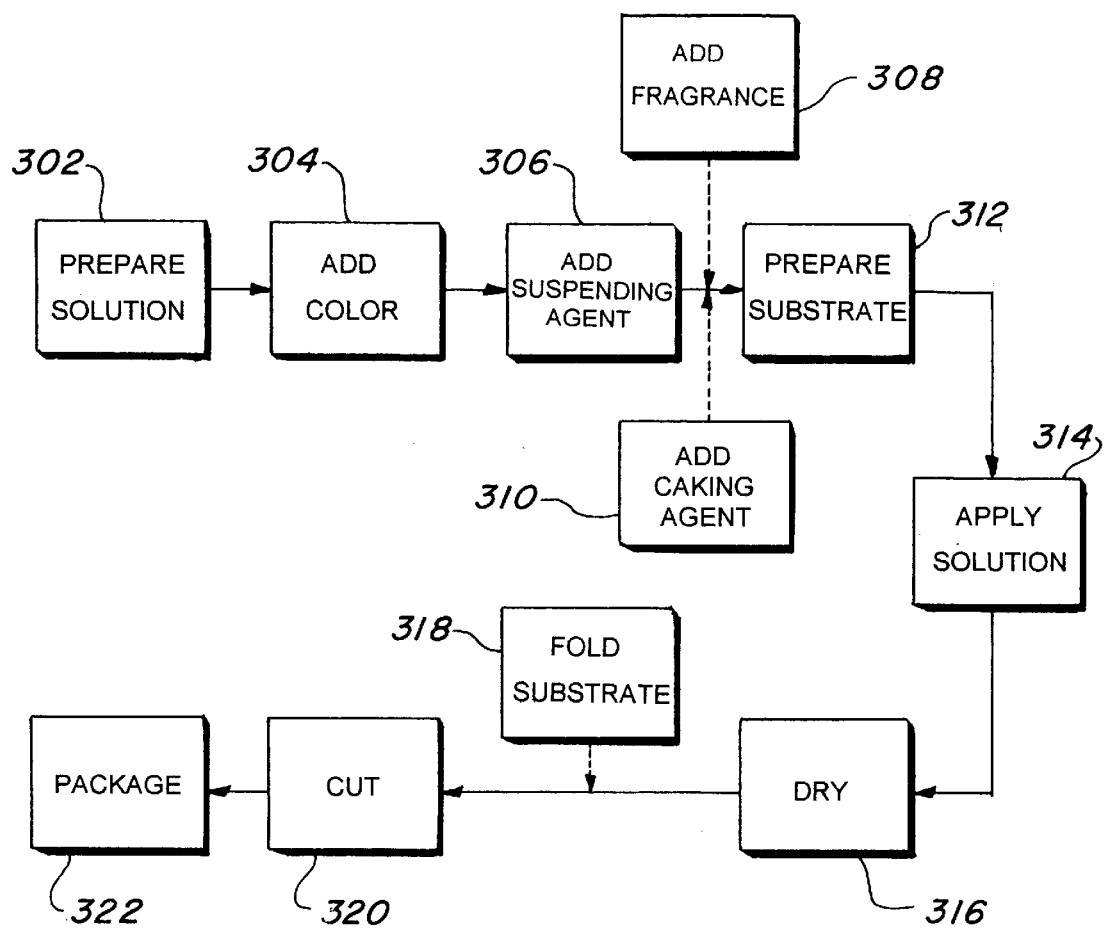
FIGS. 3 is a flow chart showing a sequence of steps of a second process for making a color applicator in accordance with the teachings of the present invention.

FIG. 3 is a block diagram showing steps contemplated by a second process of the present invention. This process involves initially forming a dye-containing solution, and then applying the solution to a substrate.

The first block 302 represents a first step of preparing a solution of water-soluble film-forming polymer in ethanol. The water-soluble film-forming polymer must be soluble in both water and alcohol, and is chosen such that it possesses a mean molecular weight of between 10,000 and 700,000. The polymer and ethanol solution is preferably prepared as a 4–31 percent wt/wt solution in ethanol, with a 4–11 percent wt/wt solution being most preferred.

Block 304 represents a second step of adding, under gentle agitation, a desired coloring compound to the polymer-ethanol solution at 15–37 percent of a known weight of the solution. This produces a suspension of coloring compound in ethanol with a concentration of 13–26 percent coloring compound.

Block 306 represents a third step of adding a suspending agent to the suspension. The suspending agent facilitates ease of handling in conventional printing processes used to deposit coloring compound on the substrate. Preferably, the suspending agent is added at a rate of 0.6–5.0 percent wt/wt of the suspension. The suspending agent maintains a homogeneous mixture of the solid coloring compound particles. The preferred concentration of suspending agent will depend on the type of printing process employed in depositing the solution on the substrate. For example, where the solution is to be deposited on a substrate using flexographic printing method, a 1.1–3.2 wt/wt percent of the color suspension is desirable.

Blocks 308 and 310 represent fourth and fifth steps of adding fragrances and a caking agent to the solution. A caking agent will allow a greater deposition of color compound during the printing process. This might be necessary for compounds that produce lighter colors. Where the use of a caking agent is indicated, a 0.4–2.3 wt/wt percent of a water insoluble/alcohol soluble oil or oily compound is preferably added.

Block 312 depicts the step of preparing the substrate for receipt of the solution. Although shown in FIG. 3 as a step following preparation of the solution, it is clear that the step of preparing the substrate can be performed before the solution is made.

The substrate to which the solution is to be applied is preferably a thin sheet of material formed from paper, plastic, plastic films, foils, webbing, etc. Preparation of the substrate includes one or more of smoothing, cleaning and drying the surface onto which the solution is to be applied. Further, the step of preparing the substrate can include the application of a moisture impermeable coating, such as wax, saran, polyester, etc. to the surface of the substrate on which the solution is to be applied. This moisture impermeable coating will prevent coloring compound from passing through the substrate and staining the user's hands or fingers.

Referring now to block 314 of FIG. 3, the process contemplates the further step of applying the solution to the substrate via conventional printing methods, such as flexographic printing, gravure, silkscreen, offset printing, web offset, etc. One method of application of the solution to the substrate is by a web offset process using a flexographic apparatus. In this method, a continuous roll of a selected paper substrate is carried on a web press which includes an in-line finishing roll.

Printing can take place on both sides of the web. On a first side of the web, the coloring compound solution is deposited. On the other side of the web, the printing can take the form of text, such as instructions for use or disposal, and/or graphics, such as the manufacturer's logo or illustrations depicting use and handling. Either side may also be provided with a colored background. The color-altering solution is preferably printed on the first side of the substrate in the form of a single strip covering an elongated region of the substrate. Where the substrate is an elongated web that is to be folded in half lengthwise, less than ½ of the web width is printed with the the coloring compound. The printed strip of coloring compound can be any width, but between ⅜" and 2" has been found preferable for economy and efficiency. Once the strip of coloring compound is applied, the substrate is immediately passed through a gas fired forced air print drier.

Figure 5:
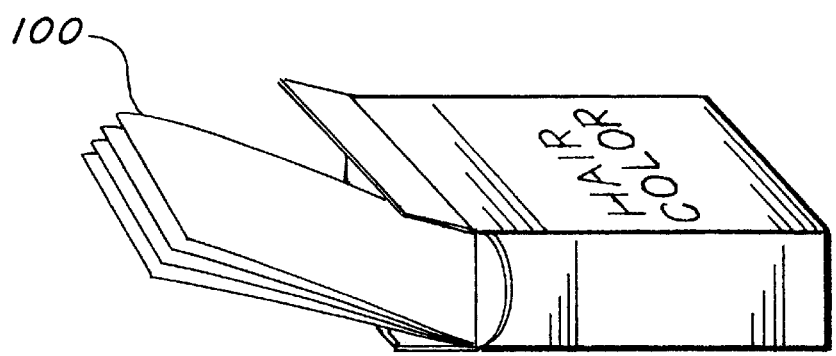
FIG. 5 shows plural applicators being inserted into a box for packaging as a kit.

When dried, the substrate may be folded (block 318) so that the hair color can be contained inside a folder. Whether or not folded, the web can then be cut (block 320) into individual pieces, and then packaged (block 322) individually or with other pieces having the same or different colors as a kit (see FIG. 5).

Figure 6:
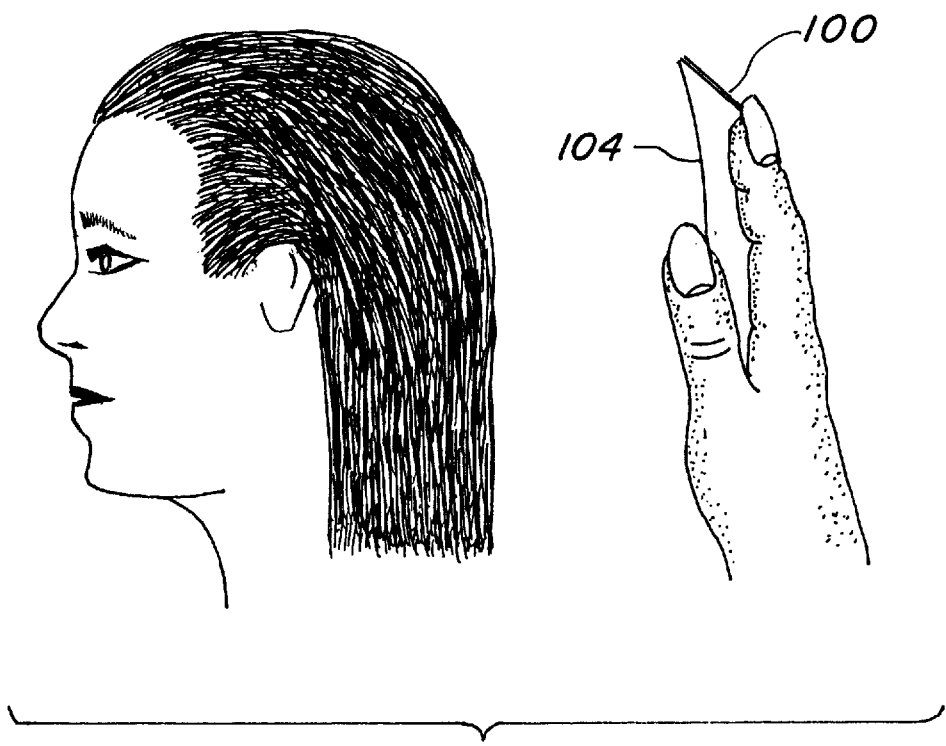
FIG. 6 shows an applicator in a user's hand while being used to color hair on another person's head.

Use of an applicator involves wetting the bundle of hairs or fibers (which have been identified for coloring), and then interposing a substrate between the user's hand and the hair or fibers to be colored, cradling the substrate in the hand so that the substrate can conform to the shape of the user's hand (see FIG. 6). Next, the user either presses the substrate against the wet hair and contemporaneously moves the substrate relative to the hair or fibers with a wiping motion, or wraps the substrate about the hair or fibers, and firmly squeezes the hair or fibers within the encircling substrate, or both.

Use of an applicator also requires that the hair or fibers first be wet, as for example with water or steam. When the substrate is pressed, or squeezed, against the hair or fibers, the coloring material and moisture are allowed to to co-mingle. This in turn causes the water-activated dye particles to mix with the water and form a dye-containing solution on the surface of the applicator adjacent the hair or fibers.

The squeezing and/or wiping motion of the substrate relative to the hair or fibers enables the dye-containing coloring compound to be transferred to the hair or fibers.

Figure 4:
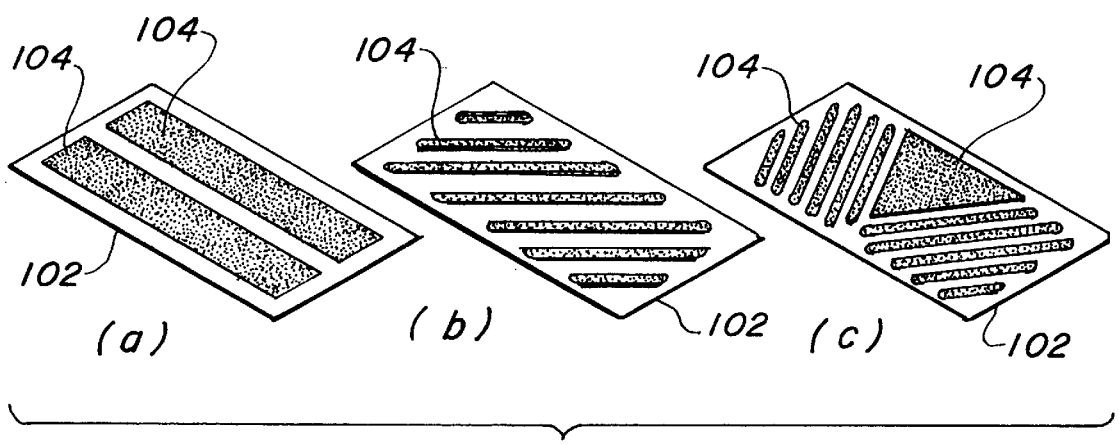
FIGS. 4a–4c show three exemplary patterns which have proven effective for coloring the bundle of hair or fibers.

The applicator and method for making such, as described above in connection with the present invention, involves the deposition of the color-altering compound solution on the substrate web in a variety of patterns and designs, by processes similar to those depicted in FIGS. 2 and 3. Three exemplary patterns are shown in FIGS. 4a (spaced rectangles), 4b (parallel lines) and 4c (chevrons). Other patterns and designs can include spaced and/or juxtaposed circles, grids, and dots. The coloring composition that can be used with the applicator of the present invention and in the methods for making the applicator include temporary, semi-permanent, or permanent hair color compounds, bleaching compounds, conditioning hair coloring compounds, etc.

While the present invention has been described in conjunction with specific embodiments thereof, it is evident that many alternatives, modifications, and variations will be apparent to those skilled in the art in light of the foregoing description. Accordingly, the present invention is intended to embrace all alternatives, modifications, and variations which fall within the spirit and scope of the appended claims.

What we claim is:

1. An applicator for transferring color-altering material to strands of hair or fibers, comprising:

a flexible substrate conformable to a human hand, water-activated color-altering material secured to said substrate and said substrate defined by a thin flat sheet member having a first portion of a first width bearing said color-altering material, and a second portion of a second width equal to said first width devoid of said solution foldable over said first portion to act as a cover for said first portion.

2. The applicator of claim 1, and further including binder material on said substrate for affixing said color-altering material to said substrate, wherein said binder material and said color-altering material are both water soluble.

3. The applicator of claim 1 wherein said color-altering material is semi-permanent hair coloring.

4. The applicator of claim 1, wherein said substrate is porous, and includes a coating of moisture-impermeable material between said color-altering material and said substrate.

5. The applicator of claim 4, wherein said color-altering material comprises one or more of a hair color, a bleaching compound, and a conditioning agent.

6. The applicator of claim 1, wherein said binder material comprises an adhesive material.

7. The applicator of claim 1, wherein said binder material is tacky and said water-activated color-altering material comprises a dry particulate, said binder material acting as a "glue" to secure said particulate to said substrate.

8. The applicator of claim 1, wherein said binder material comprises a polymer having a mean molecular weight of between 10,000 and 700,000.

9. The applicator of claim 8, wherein said polymer adheres to both said water-activated color-altering material and said substrate, said polymer being water soluble, and therefore able to release said color-altering material when contacted with water.

10. AThe applicator of claim 1 wherein said color-altering material is permanent hair coloring.

11. A method of making an applicator for coloring fibers, comprising the steps of:

providing a flexible substrate having first and second surfaces opposing one another, adhering water-activated color-altering material to said first surface of said substrate and folding said substrate to provide a first region of said substrate on which said color altering material is applied, and a second region devoid of said color-altering material.

12. The method of claim 11, wherein said step of adhering color-altering by material to said substrate first surface comprises first applying a binder material to said first surface.

13. The method of claim 12, including the further step of cutting said substrate into segments.

14. The method of claim 13, including the further step of packaging at least one of said segments in a container.

15. The method of claim 12, wherein the step of adhering comprises printing said color-altering material on said first surface.

16. If The method of claim 12, wherein said step of applying a binder material to said first surface comprises spraying a tacky substance on said application surface.

17. The method of claim 16, wherein said step of applying a binder material further comprises the steps of depositing said color-altering material atop said binder material and then drying said binder material.

18. The method of claim 11, and including the further step, before adhering said color-altering material on said substrate, of preparing a solution of water-soluble film forming polymer in ethanol, where the polymer possesses a mean molecular weight of between 10,000 and 700,000.

19. The method of claim 18, and further including the step of adding the color-altering material to said solution.

20. The method of claim 19, and further including the step of adding a suspending agent to said solution.

21. The method of claim 20, and further including the steps of adding a caking agent to said solution.

22. The method of claim 20, and further including the step of of adding fragrance to said solution.

23. The method of claim 20 and further including the step of adding a caking agent and fragrance to said solution.

24. The method of claim 11 wherein said color-altering material is semi-permanent hair coloring.

25. The method of claim 11 wherein said color-altering material is permanent hair coloring.

26. A hair color kit, comprising:

a package, a set of applicators, located in said package, for transferring coloring material to strands of hair or similar fibers, each of said applicators including a flexible substrate conformable to a human hand, water-activated color-altering material secured to said substrate, and said substrate defined by a thin flat sheet member having a first portion of a first width bearing said color-altering material and a second portion of a second width equal to said first width devoid of said color-altering material and foldable over said first portion to act as a cover for said first portion.

27. The hair color kit of claim 26, wherein the coloring material of each of said applicators is a different shade of hair color.

28. A method for coloring hair, comprising the steps of:

wetting the hair, contacting the wet hair with a substrate bearing water-soluble hair dye, providing said flexible substrate with a first and a second surface opposing one another, adhering said water soluble hair dye to said first surface of said substrate, folding said substrate to provide a first region of said substrate on which said hair dye is applied, and a second region devoid of said hair dye, and maintaining contact between the wet hair and the substrate long enough to transfer the hair dye from said substrate to said hair.

29. The method of claim 28, wherein said step of contacting said wet hair comprises moving the substrate relative to said hair so that said transfer of hair dye to said hair can be effected.

30. The method of claim 29, wherein said substrate is a thin, flexible sheet that is conformable to a human hand, and said method further comprises the further steps of grasping a bundle of hair fibers so that said substrate encircles said bundle, and squeezing said bundle encircled by said substrate.

* * * * *